(12) United States Patent
Alakhov et al.

(10) Patent No.: US 6,218,438 B1
(45) Date of Patent: Apr. 17, 2001

(54) COPOLYMER COMPOSITIONS FOR TREATING VIRAL INFECTIONS

(75) Inventors: Valery Alakhov, Baie d'Urfe (CA); Alexander Kabanov, Omaha, NE (US); Michael Parniak, Verdu n; Evgueni Klinski, Laval, both of (CA)

(73) Assignee: Supratek Pharma, Inc., Monreal (CA)

( * ) Notice: Subject to any disclaimer, the term of this patent is extended or adjusted under 35 U.S.C. 154(b) by 0 days.

(21) Appl. No.: 09/442,225

(22) Filed: Nov. 17, 1999

Related U.S. Application Data

(60) Provisional application No. 60/108,975, filed on Nov. 18, 1998.

(51) Int. Cl.[7] .......................... A61K 47/32; A61K 31/295

(52) U.S. Cl. ......................................... 514/772.4; 514/502

(58) Field of Search .................................. 514/772.4, 502

(56) References Cited

PUBLICATIONS

Borkow et al., "Inhibition of the ribonuclease H and DNA polymerase activites of HIV–1 reverse–transcriptase by N (4–tert–Butylbenzoyl)–2–hydroxy–12–naphthaldehyde hydrazone" Biochemistry 36:3179–85 (1997).*

Borkow, G. et al., "Inhibition of the ribonuclease H and DNA polymerase activites of HIV–1 reverse transcriptase by N–(4–tert–Butylbenzoyl)–2–hydroxy–1–naphthaldehyde hydrazone" Biochemistry 36:3179–85 (1997).

* cited by examiner

*Primary Examiner*—Thurman K. Page
*Assistant Examiner*—Blessing Fubara
(74) *Attorney, Agent, or Firm*—Mathews, Collins, Shepherd & Gould

(57) ABSTRACT

Compositions for delivery having a biological agent or derivative thereof, and a poly(oxyethylene)-poly(oxypropylene) block copolymer. The compositions are useful in immunodeficiency infection virus therapy. The invention also encompasses methods of treatment using the same.

8 Claims, No Drawings

COPOLYMER COMPOSITIONS FOR TREATING VIRAL INFECTIONS

CROSS-REFERENCE TO RELATED APPLICATIONS

This application claims priority from the provisional patent application, serial number 60/108,975 filed on Nov. 18, 1998, the disclosures of which are incorporated herein by reference.

FIELD OF THE INVENTION

Copolymer pharmaceutical compositions useful in the therapies of retroviral infections, including, immunodeficiency virus infections (HIV) such as HIV-1 infections.

The compositions have improved therapeutic indexes, reduction of side effects, and reduced treatment costs, and can be used to treat a variety of infectious diseases induced by viruses, bacteria and parasites, including HIV, MLV, HTLV, *E. coli*, micobacteria, RNAse H, and other metal-dependant enzymes which play an important role in reproduction of a pathogen.

BACKGROUND OF THE INVENTION

Infection by the human immunodeficiency virus (HIV) leads to AIDS, an incurable and inevitably fatal disease. A variety of biological agents are currently in use for the treatment of HIV-1 infections (Chaudry M N, and Shepp D H, *Dermatol Clin*. 15:2, 319–29 (1997); Beach J W, *Clin Ther*, 1998 January–February, 20:1, 2–25. HIV is a retrovirus and carries its genetic information as RNA. After infection, this viral genomic RNA must be converted into viral DNA. Multiple steps are involved in this crucial step of HIV replication, each of which is catalysed by the viral enzyme reverse transcriptase (RT) (Arnold, E. et al., *Drug Des. Discov.*, 1996 April, 13:3–4, 29–47). RT has three enzymatic activities, RNA-dependent DNA polymerase activity (RDDP), ribonuclease H activity (RNase H), and DNA-dependent DNA polymerase activity (DDDP). With no mammalian counterpart, RT is an important target for antiviral development. Many such inhibitors have been discovered, including dideoxynucleosides (ddN) such as 3'-azido-3'-deoxythymidine (AZT) and 2',3'-dideoxy-3'-thiacytidine (3TC) and nonnucleoside inhibitors (NNI) such as nevirapine, quinoxalines, pyridinones and BHAP. Virtually all of these inhibitors are directed against the RDDP and/or DDDP activity of RT.

Once viral DNA synthesis is complete, the viral DNA is integrated into the infected host cell's DNA, in a reaction catalyzed by the viral enzyme integrase (IN). This proviral DNA encodes the genetic information to produce new HIV virions (virus particles), and is inaccessible to antiviral intervention in this state.

Cellular machinery is used to synthesize new HIV RNA and proteins from the genetic information in the proviral DNA. These viral components assemble at the cell plasma membrane, and the nascent virions are shed from the cell. Nascent HIV virions assemble in an "immature" form; viral maturation takes place during and after virion shedding. This maturation involves proteolytic processing of virion proteins, a process, which is carried out by the HIV protease. Immature HIV virions are noninfectious, thus the HIV protease has proven to be another important target for antiviral intervention. Inhibitors of HIV protease include saquinavir, indinavir and ritonavir.

The steps of HIV replication up to the formation of proviral DNA can be considered "pre-integrational" stages, and those involved in the formation of nascent virions after integration of proviral DNA can be considered as "post-integrational." Current chemotherapy of HIV-infected individuals utilizes combinations of RT inhibitors and HIV protease inhibitors. Clinical efficacy of these combinations is due in part to inhibition at both pre-integrational stages (RT) and post-integrational stages (protease) of HIV replication (McIntosh E M, et al., Acta Biochim Pol, 1996, 43:4, 583–92).

A number of antiviral agents exhibit low solubility and stability in physiological fluids. Often, chemotherapeutic agents are poorly transported across cell membranes. Further, many of these agents are binding with plasma proteins as well as other nonspecific interactions in the blood stream before they can reach the pharmacological target. Additionally, there is another serious problem associated with current anti-HIV chemotherapeutics. Although treatment with currently approved antivirals initially improves the quality of life and longevity of HIV-infected patients, prolonged therapy inevitably leads to drug-resistance (Kuritzkes D R, AIDS, Dec. 10, 1996 Suppl 5: S27–31; Richman D D, Adv Exp Med Biol, 1996, 394: 383–95). Resistance to RT inhibitors correlates with mutations in RT, and resistance to protease inhibitors correlates with mutations in the HIV protease. Clinical appearance of drug-resistant HIV imparts an unfavourable prognosis.

SUMMARY OF THE INVENTION

The present invention relates, among other things, to (1) pharmaceutical compositions and methods for chemotherapeutic agents and (2) pharmaceutical compositions for anti HIV-1 agents, particularly those, whose target cells or tissues are resistant to the biological agent.

The present invention thus relates to compositions for HIV therapy comprising metal and metal-chelating agent (hereinafter-biological agent, or biologically active agent).

In one embodiment, the invention provides a pharmaceutical composition comprising:

(a) a biological agent which is the metal complex of an N-aroyl hydrazone of the general structure (I):

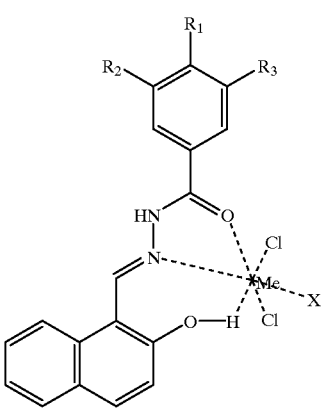

where $R_1$, $R_2$, and $R_3$ are H, OH, $CH_3$, $OCH_3$, $C(CH_3)_3$ [-tert-butyl], or phenyl, and X is $OCH_3$, or $OCH_2CH_3$. The metal (Me) is any metal that can be chelated by the compound I, for example, Fe(II), Fe(III), Mn(II), Co(II), Mg(II), etc., preferably Fe(III).

In the most preferable form, $R_1$ is $C(CH_3)_3$, $R_2$ and $R_3$ are H, Me is Fe(III), and X is $OCH_3$.

The invention may incorporate the use of block copolymers. Some block copolymer architectures are presented below.

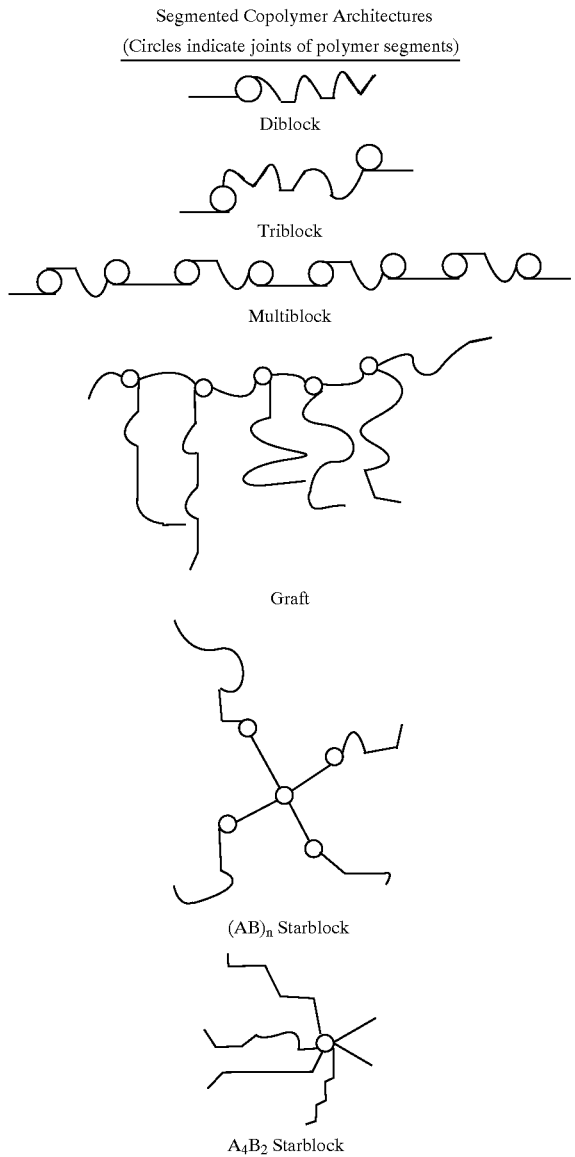

The simplest block copolymer architecture contains two segments joined at their termini to give an A—B type diblock. Consequent conjugation of more than two segments by their termini yields A—B—A type triblock, A—B—A—B— type multiblock, or even multisegment A—B—C— architectures. If a main chain in the block copolymer can be defined in which one or several repeating units are linked to different polymer segments, then the copolymer has a graft architecture of, e.g., an $A(B)_n$ type. More complex architectures include for example (AB)n or $A_nB_m$ starblocks which have more than two polymer segments linked to a single center.

In a preferred embodiment, the biological agent is combined with a surfactant that improves solubility of the biological agent and/or its intracellular transport. Preferred surfactants are nonionic or zwitterionic. Preferred nonionic surfactants have block, graft, or starblock copolymer architecture. Preferred block copolymers comprise poly (oxyethylene) and poly(oxypropylene) chain segments. Additionally preferred are compositions wherein the surfactant has a critical micellar concentration ("CMC") of about 0.5% wt/vol. or less at 37° C. in an isotonic aqueous solution.

In another embodiment, the invention provides a method of targeting a biological agent to a pre-selected tissue. The method comprises administering the composition described above, wherein the targeting moiety is selected to target the tissue, to an animal having the pre-selected tissue.

In yet another embodiment, the invention relates to compositions for the delivery of biologically active agent comprising a poly(oxyethylene)-poly(oxypropylene) block copolymer and a biologically active agent, or derivative thereof, wherein the hydrophobe percentage of the poly (oxyethylene)-poly(oxypropylene) block copolymer is about 50%.

Preferred block copolymers are of the formula:

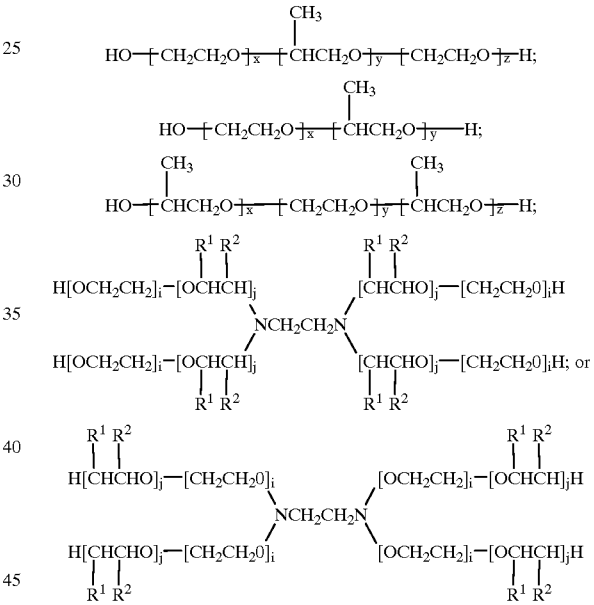

in which x, y, z, i, and j have values from about 2 to about 800, and wherein for each $R^1$, $R^2$ pair, one is hydrogen and the other is a methyl group.

In another preferred embodiment, the invention relates to compositions for the delivery of a biologically active agent, or derivative thereof, comprising a biologically active agent, or derivative thereof, and a block copolymer of the formula:

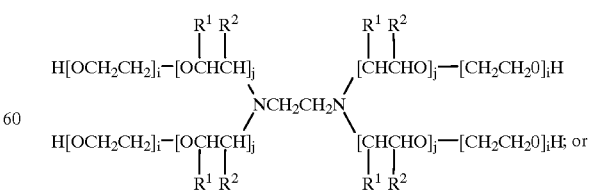

-continued

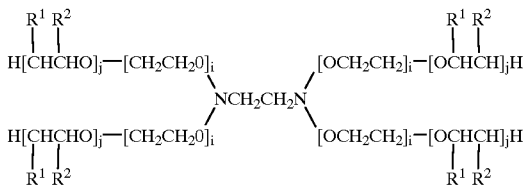

wherein for each $R^1$, $R^2$ pair, one is hydrogen and the other is a methyl group.

In another preferred embodiment, the invention relates to compositions for the delivery of a biologically active agent, or derivative thereof comprising a biologically active agent, or derivative thereof, and a block copolymer of the formula:

in which x, y, and z have values from about 2 to about 800.

The invention also relates to methods of treating infection, including HIV-1 infections, using these compositions.

DETAILED DESCRIPTION OF THE INVENTION

Definitions

The terms or phrases used herein have the following meaning:

Biological agent: The metal complex of an N-aroyl hydrazone of the general structure illustrated as I:

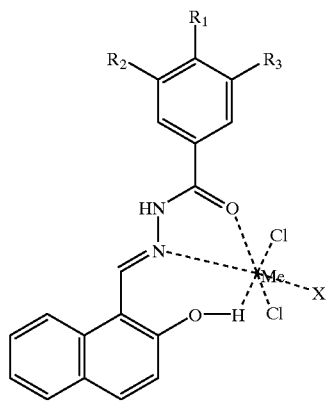

CC$_{50}$: The concentration at which 50% cytotoxic effect is noted. Cytotoxicity for antiviral compounds refers to toxicity arising from the drug itself, as opposed to cytopathicity, which is cell death arising from viral infection.

Chronically-infected cells: Also known as 'persistently-infected' cells; cells which have been infected with HIV, contain proviral DNA integrated into cell DNA and continually produce new virus particles. These cells do not exhibit overt cytopathic effects due to HIV infection.

Cytopathic effect: Cell killing and cell death due to HIV infection

Hydrophobe percentage: The percentage of the molecular weight of a block copolymer that is made up of B-type blocks.

Hydrophobe weight: The molecular weight contribution of the B-type blocks of a block copolymer.

IC$_{50}$: The concentration at which 50% inhibitory effect is obtained.

Lipophilic moiety: A lipophilic substituent that is joined to a targeting moiety and that partitions into the lipophilic portion of copolymer micelles.

Provirus: Viral DNA which has been integrated into the infected host cell's genomic DNA.

Resistance: On the viral level, resistance is the lack of responsiveness of HIV to antiviral agents, arising from mutations in specific viral genes. On the cellular level, the phenomenon of simultaneous resistance to biological agents.

Syncytium: Formation of giant multinucleated cells due to HIV-infection induced cell fusion.

Targeting moiety: A molecular structure that is recognized by a cellular, tissue, viral or substratum component such as a cell surface receptor or acceptor molecule.

The present invention relates among other things to pharmaceutical compositions and methods for biological agents particularly those, whose target cells or tissues are infected with HIV-1. Many human cell types are susceptible to HIV infection, but the extent of infection varies greatly depending on cell type. In general, cells that possess CD4 receptors (CD4+ cells) are the most readily infected and most permissive for HIV replication. Such cells include, for example, T-lymphocytes and macrophages.

A variety of permanent established cell lines of lymphocyte and monocyte/macrophage derivation can be used to propagate and maintain HIV in in vitro culture. These include the CD4+ MT2, and MT4 cell lines, which are cloned human T-lymphocytic cells isolated from adult T-cell leukemia patients. These cells are highly susceptible to HIV-induced cytopathic effects, and are useful for acute infection cytopathicity inhibition assays for antiviral drugs.

Other cells include the cloned H9 cell line, derived from a human cutaneous T-lymphoma patient. See Mann, D L et al., *AIDS Res Hum Retroviruses* 5:253 (1989). H9 cells are CD4+ and permissive for HIV infection, but are relatively non-susceptible to HIV-induced cytopathic effects. Once infected with HIV, these cells continuously produce new virus without succumbing to the infection. These infected cells, H9+, are said to be "chronically-infected", or "persistently-infected."

The steps of HIV replication up to the formation of proviral DNA can be considered "pre-integrational" stages, and those involved in the formation of nascent virions after integration of proviral DNA can be considered as "post-integrational." The MT2 and MT4 cell lines are useful to assess antiviral activity against preintegrational stages of HIV replication (in particular, effects on viral reverse transcription). The H9+ cells are useful to examine antiviral activity against post-integrational stages of HIV replication, including effects on virus assembly, shedding and maturation.

HIV-infected patient body fluids, such as blood, seminal and vaginal fluids, contain not just free virions, but also virus-infected leukocytes (including lymphocytes and macrophages). See, Levy, J. A. *Microbiol. Rev.* 57: 183 (1993). These HIV-infected cells are a significant source for viral transmission to uninfected cells (both within an already-infected individual, and from an infected person to a previously noninfected individual). Such transmission of infection may be due to exposure to free HIV virions produced from the chronically-infected cells, or to contact between the persistently-infected cell with an uninfected cell (cell-to-cell transmission). Co-culture of H9+ cells with uninfected MT2 cells is a useful means to assess the effect of antiviral agents on inhibition of cell-to-cell transmission of HIV.

Compositions of the present invention can also be used to enhance drug permeability into HIV-1 infected cells.

Biologically Active Agents

Uncomplexed parent N-aroyl hydrazone, N-(4-t-butylbenzoyl)-2-hydroxy-1-naphthaldehyde hydrazone (BBNH; II) is a good inhibitor of all three enzymatic activities of HIV-1 RT in vitro (RDDP, RNase H, and DDDP), and inhibits replication of HIV-1 in infected cells. See, Borkow et al., *Biochemistry* 36: 3179 (1997).

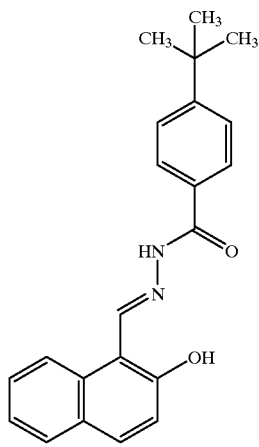

BBNH also inhibits the DNA-binding activity of HIV IN ($IC_{50} \approx 5$ μM) in vitro. However, there are problems with BBNH as an inhibitor of HIV-1 replication. Inhibition of both RT RNase H and IN in vitro is a time-dependent process, with maximal inhibition noted only after 10–15 minutes preincubation of the enzyme with BBNH. This requirement for preincubation diminishes the utility of the compound as an inhibitor of RT RNase H and/or IN in HIV-infected cells. In addition, BBNH is cytotoxic, possibly due to interaction of this broad specificity metal chelator with enzymes involved in normal cellular metal-dependent metabolism.

The Fe(III) complex of BBNH shows improved inhibitory activity compared to the parent uncomplexed BBNH against RT in vitro. Fe(III)-BBNH has virtually no cytotoxicity; however, the compound also shows no antiviral activity against HIV-1 replication in cells, despite excellent in vitro inhibition of RT. Fe(III)-BBNH is also practically insoluble in a water medium and requires the use of organic solvents to deliver the compound to infected cells. While such an approach is applicable to in vitro tests, it cannot be used in vivo for chemotherapeutic purposes. Furthermore, even in in vitro experiments to test the ability of Fe(III)-BBNH to inhibit HIV-1 replication in cells, in which water-organic formulations of Fe(III)-BBNH, the compound showed very low activity. This is likely due to the inability of Fe(III)-BBNH to remain in soluble form in cell culture medium with resulting limited cellular uptake of the complex. Fe(III)-BBNH is therefore unable to reach its viral target in infected cells.

A variety of biological agents are suitable for use in the invention. These include, without limitation, compounds of the class of N-aroyl hydrazones in 1:1 complex with a metal such as Fe(III), as illustrated for structure I:

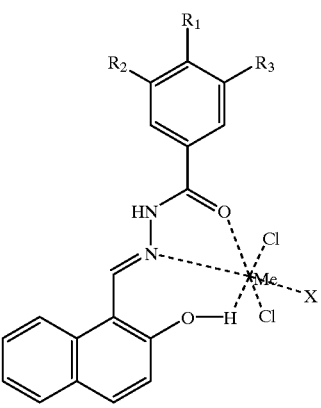

where $R_1$, $R_2$, and $R_3$ are H, OH, $CH_3$, $OCH_3$, $C(CH_3)_3$ [-tert-butyl], or phenyl, and X is $OCH_3$ or $OCH_2CH_3$. Me is preferably Fe(III). More preferred forms are those in which $R_1$ is $C(CH_3)_3$, $R_2$ and $R_3$ are H, Me is Fe(III), and X is $OCH_3$.

The biological agents may also include compounds of the class of N-aroyl hydrazones in 1:1 complex with a metal such as Fe(III), as illustrated for structure III:

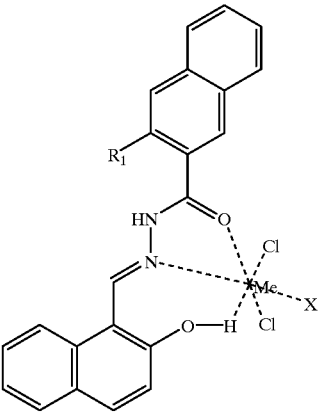

where $R_1$ is H, OH, $CH_3$, or $OCH_3$, and X is $OCH_3$ or $OCH_2CH_3$. The preferred Me is Fe(III). In the most preferable form, $R_1$ is OH, Me is Fe(III), and X is $OCH_3$.

Block Copolymers

Recent observations described in more detail in U.S. application Ser. No. 08/478,978 filed Jun. 7, 1995, entitled "Biological Agent Compositions", the contents of which are incorporated herein, demonstrate the effectiveness of the block copolymers of the invention in enhancing the potency of chemotherapeutic drugs is highly dependent (a) on the hydrophobe percentage and (b) on the hydrophobe weight. The effectiveness increases with either an increase in the percentage (a) or an increase in weight (b), or both. These hydrophobe percentage and hydrophobe weight increases also correlate with improved micelle formation properties wherein micelle formation for these copolymers occurs at lower concentrations. See, Hunter et al., Macromolecules 26:5030 (1993); Hunter et al., Macromolecules 26:5592 (1993); Alexandris et al., Macromolecules 27:2414 (1994).

While not wishing to be limited to a particular theory, it is believed that micelle formation serves as a surrogate for measuring the physical properties that lead to improved biological agent delivery properties. Again, not wishing to be limited to a particular theory, it is believed that it is not micelles per se that lead to improved biological agent efficiency and reversion of multidrug resistance.

The effectiveness of copolymers in (a) forming micelles (where greater effectiveness is measured in reduced CMCS) and (b) favoring the partitioning of various biological agents to the micellar rather than the free form of various biological agents increases according to the same pattern. The presence of micelles at low concentrations is believed to help assure, assuming that biological agent remains associated with the micelles, that the biological agent and the copolymer arrive together at a target tissue. Partitioning coefficients that favor the micellar form help assure that the assumption that the biological agent remains associated with micelles will hold true. The micellar form of the biological agent is also believed to protect the biological agent from uptake by non-target tissues, which tissues may metabolize the biological agent into an ineffective or toxic metabolite, and non-specific adsorption to blood components, cellular components and the like.

The compositions of the invention also include either preformed micelles with a substantial portion of the biological agent incorporated therein, or copolymer compositions which form micelles with a substantial portion of the agent dissolved therein during the course of the administration of the biological agent to a patient, or subsequent thereto. For targeting embodiments of the invention, the targeting moiety will either be pre-associated with micelles or will associate with micelles during the course of administration. Particularly preferred block copolymers are those that have low CMC values in isotonic solutions at physiological temperatures. Such block copolymers will maintain a micellar delivery vehicle for biological agents even after substantial dilution into a physiological fluid such as a treatment subject's blood. Such low CMC values allow for the use of reduced levels of block copolymers in the drug composition of the invention.

The invention can also be described with reference to the fragmental constants developed by Hansch and Leo. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. These constants were developed for use in estimating the contribution of a portion of a molecule to the tendency of the molecule to partition between the phases formed by octanol-water mixtures. These constants are generally referred to as Hansch-Leo fragmental partition constants (hereinafter "Hansch-Leo fragmental constants").

The Hansch-Leo estimate of the octanol-water partitioning coefficient (P) for an organic molecule is calculated by the following formula:

$$\text{Log } P=a_n f_n+\Sigma b_m F_m$$

where the $f_n$ values are the fragmental constants for the different groups in the molecule, the an values are the number of any type of group in the molecule, the FM values are factors for certain molecular features such as single bonds or double bonds, and the bm values are the number of any such molecular feature. For instance, the Hansch-Leo fragmental constant for an ethylene oxide repeating unit ($—CH_2CHO—$) would be:

$$2f_c+4f_H+f_o+(4-1)F_b=2(0.20)+4(0.23)+(-1.82)+3(-0.12)=-0.86$$

The Hansch-Leo fragmental constant for a propylene oxide ($—CH_2CH(CH_3)O—$) repeating unit would be:

$$2f_c+f_{CH3}+3fH+f_o+(4-1)F_b=2(0.2)+0.89+3(0.23)+(-0.12)=0.86$$

Those of ordinary skill in the art will recognize that the Hansch-Leo approach to estimating partition constants, in which approach the Hansch-Leo fragmental constants are applied, does not yield precisely the empirical partition constant. See Hansch and Leo, *Substituent Constants for Correlation Analysis in Chemistry and Biology*, Wiley, New York, 1979; James, *Solubility and Related Properties*, Marcel Dekker, New York, 1986, pp. 320–325. However, the approach is precise enough to define the hydrophobicity features of the polymeric delivery vehicle.

The entire disclosure of U.S. patent application Ser. No. 08/478,978 filed Jun. 7, 1995, U.S. patent application Ser. No. 08/054,403, filed Apr. 28, 1993, Ser. No. 09/019,648, filed Feb. 6, 1998, and Ser. No. 09/031,279, filed Feb. 27, 1998 are hereby incorporated by reference.

Preferred block copolymers useful in this invention are selected from the group consisting of polymers of formulas:

| A-B-A', (IV-a) | A-B, (IV-b) | B-A-B', (IV-c) | or L(R')($R^2$) ($R^3$) ($R^4$) (IV-d) |
|---|---|---|---| where A and A' are A-type linear polymeric segments, B and B' are B-type linear polymeric segments, and $R^1$, $R^2$, $R^3$, and $R^4$ are either block copolymers of formulas (I), (II), or (III), or hydrogen and L is a linking group, with the proviso that no more than two of $R^1$, $R^2$, $R^3$, or $R^4$ are hydrogen.

The numbers of repeating units of the total hydrophilic (A-type) blocks or the total hydrophobic (B-type) blocks for a polyether copolymer are preferably between about 2 and about 800. More preferably, the number of repeating units is between about 4 and about 200, still more preferably, between about 5 and about 80. The repeating units that comprise the blocks, for A-type and B-type blocks, will generally have molecular weight between about 30 and about 500, preferably between about 30 and about 100, still more preferably between about 30 and about 60. Generally, in each of the A-type or B-type blocks, at least about 80% of the linkages between repeating units will be ether linkages, preferably, at least about 90% will be ether linkages, more preferably, at least about 95% will be ether linkages. Ether linkages, for the purposes of this application, encompass glycosidic linkages (i.e., sugar linkages). However, in one aspect, simple ether linkages are preferred.

Preferably, all of the repeating units that comprise A-type blocks have a Hansch-Leo fragmental constant of less than about −0.4, more preferably, less than about −0.5, still more preferably, less than about −0.7. Preferably, all of the repeating units that comprise B-type blocks have a Hansch-Leo fragmental constant of about −0.30 or more, more preferably about −0.20 or more.

Polymers according to the first embodiment of the invention are exemplified by the block copolymers having the formulas:

(V)

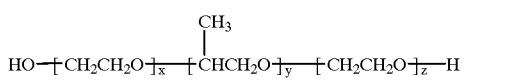

(VI)

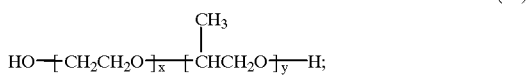

(VII)

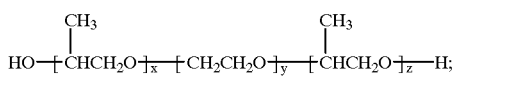

(VIII)

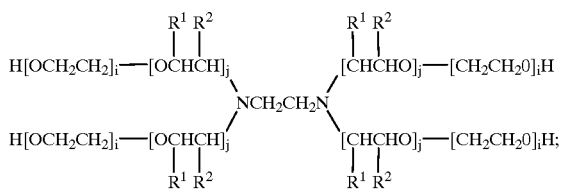

or (IX)

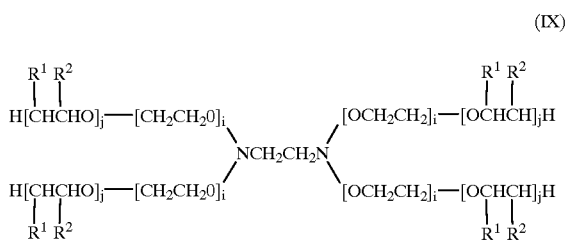

in which x, y, z, i, and j have values from about 2 to about 800, preferably from about 5 to about 200, more preferably from about 5 to about 80, and wherein for each $R^1$, $R^2$ pair, one is hydrogen and the other is a methyl group. Formulas (V) through (VII) are oversimplified in that, in practice, the orientation of the isopropylene radicals within the B block will be random. This random orientation is indicated in formulas (VIII) and (IX), which are more complete. Such poly(oxyethylene)-poly(oxypropylene) compounds have been described by Santon, *Am. Perfumer Cosmet.*, 72(4):54–58 (1958); Schmolka, *Loc. cit.* 82(7):25–30 (1967); *Non-ionic Surfactants*, Schick, ed. (Dekker, N.Y., 1967), pp. 300–371. A number of such compounds are commercially available under such generic trade names as "lipoloxamers," "pluronics," and "synperonics." Pluronic polymers within the B—A—B formula are often referred to as "reversed" pluronics, "pluronic R" or "meroxapol."

The "polyoxamine" polymer of formula (VIII) is available from BASF (Wyandotte, Mich.) under the tradename Tetronic™. The order of the polyoxyethylene and polyoxypropylene blocks represented in formula (VIII) can be reversed, creating Tetronic R™, also available from BASF. See, Schmolka, *J. Am. Oil. Soc.*, 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

The hydrophobic/hydrophilic properties of a given block copolymer depends upon the ratio of the number of oxypropylene groups to the number of oxypropylene groups. For a composition containing a single block copolymer of poly (oxyethylene)poly(oxypropylene), for example, this relationship, taking into account the molecular masses of the central hydrophobic block and the terminal hydrophilic blocks, can be expressed as follows:

$$n = H/L \cdot 1.32$$

in which H is the number of oxypropylene units and L is the number of oxyethylene units. In the general case of a block copolymer containing hydrophobic B-type segments and hydrophilic A-type segments, the hydrophobic-hydrophilic properties and micelle-forming properties are related to the value n as defined as:

$$n = (|B|/|A|) \times (b/a)$$

where $|B|$ and $|A|$ are the number of repeating units in the hydrophobic and hydrophilic blocks of the copolymer, respectively, and b and a are the molecular weights for the respective repeating units.

Selecting a block copolymer with the appropriate n value depends upon the hydrophobic/hydrophilic properties of the specific agent, or the composite hydrophilic/hydrophilic properties of a mixture of agents to be formulated. Typically, n will range in value from about 0.2 to about 9.0, more preferably between about 0.25 and about 1.5. This range should be viewed not as numerically critical but as expressing the optimum hydrophobic/hydrophilic balance between the predominantly hydrophilic poly(oxyethylene) blocks, and the predominantly hydrophobic poly(oxypropylene) blocks.

An important aspect of the present invention-involves utilizing mixture of different block-copolymers of poly (oxyethylene)-poly(oxypropylene) to achieve a more specific hydrophobic-hydrophilic balance suitable for a given biological agent, preserving the optimal size of particles. For example, a first block copolymer may have an n of 1.0 whereas a second may have a value of 1.5. If material having an n of 1.3 is desired, a mixture of one weight portion of the first block copolymer and 1.5 weight portion of the second block-copolymer can be employed.

Thus, a more generalized relationship for such mixtures can be expressed as follows:

$$N = 1.32 \cdot \left[ \frac{H_1 \cdot m_1}{(L_1) \cdot (m_1 + m_2)} + \frac{H_2 \cdot m_2}{(L_2) \cdot (m_1 + m_2)} \right]$$

in which $H_1$ and $H_2$ are the number of oxypropylene units in the first and second block copolymers, respectively; $L_1$ is the number of oxyethylene units in the first block copolymer; $L_2$ is the number of oxyethylene units in the second block copolymer; $m_1$ is the weight proportion in the first block-copolymer; and m2 is the weight proportion in the second block copolymer.

An even more general case of a mixture of K block copolymers containing hydrophobic B-type block copolymers and hydrophilic A-type block copolymers, the N value can be expressed as follows:

$$N = \frac{b}{a} \sum_{i=1}^{k} \left( \frac{|B|_i}{|A|_i}, \frac{m_i}{M} \right)$$

where $|A|_i$ and $|B|_i$ are the numbers of repeating units in the hydrophilic (A-type) and hydrophobic (B-type) blocks of the i-th block copolymer, m is the weight proportion of this block copolymers, M is the sum of weight proportions of all block copolymers in the mixture $$\left(M = \sum_{i=1}^{k} m_i\right),$$

and a and b are the molecular weights for the repeating units of the hydrophilic and hydrophobic blocks of these block copolymers respectively.

If only one block copolymer of poly(oxyethylene)-poly(oxypropylene) is utilized, N will equal n. An analogous relationship will apply to compositions employing more than two block copolymers of poly(oxyethylene)-poly(oxypropylene).

Where mixtures of block copolymers are used, a value N will be used, which value will be the weighted average of n for each contributing copolymers, with the averaging based on the weight portions of the component copolymers. The value N can be used to estimate the micelle-forming properties of a mixture of copolymers. The use of the mixtures of block copolymers enhances solubility and prevents aggregation of more hydrophobic block copolymers in the presence of the serum proteins. Particularly, poly(oxyethylene)-poly(oxypropylene) block copolymers with the ethylene oxide content of more than 50% solubilize hydrophobic block copolymers with ethylene oxide content of no more than 50%. In such mixtures, the preferred ratio of the hydrophilic and hydrophobic copolymer is at least 2:1 (w/w), preferably at least 5:1 (w/w), still more preferably at least 8:1 (w/w)." When copolymers other than polyethylene oxide-polypropylene oxide copolymers are used, similar approaches can be developed to relate the hydrophobic/hydrophilic properties of one member of the class of polymers to the properties of another member of the class.

Using the above parameters, one or more block copolymers of poly(oxyethylene)-poly(oxypropylene) are combined so as to have a value for N of from about 0.1 to about 9, more preferably from about 0.25 to about 1.5. The combined copolymers form micelles, the value of N affecting in part the size of the micelles thus produced. Typically the micelles will have an average diameter of from about 10 to about 25 nm, although this range can vary widely. The average diameter of any given preparation can be readily determined by quasi-elastic light scattering techniques.

A number of pluronics are designed to meet the following formula:

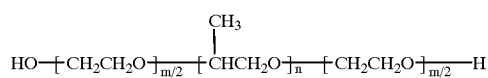

(X)

Of course, the ordinarily skilled artisan will recognize that the values of m and n will usually represent a statistical average and that the number of repeating units of the first block of a given molecule will generally not be exactly the number of repeating units of the third block. The characteristics of a number of block copolymers, described with reference to formula (X), are as follows:

| Copolymer | MW | Average no. of oxypropylene units, n | Average no. of oxyethlene units, n | HLB | CMC, $\mu M^c$ |
|---|---|---|---|---|---|
| L31 | 1100 | 17.1 | 2.5 | 5 | 1180 |
| L35 | 1900 | 16.4 | 21.6 | 19 | 5260 |
| L43 | 1850 | 22.3 | 12.6 | 12 | 2160 |
| L44 | 2200 | 22.8 | 20.0 | 16 | 3590 |
| L61 | 2000 | 31.0 | 4.5 | 3 | 110 |
| L62 | 2500 | 34.5 | 11.4 | 7 | 400 |
| L64 | 2900 | 30.0 | 26.4 | 15 | 480 |
| F68 | 8400 | 29.0 | 152.7 | 29 | 480 |
| L81 | 2750 | 42.7 | 6.2 | 2 | 23 |
| P84 | 4200 | 43.4 | 38.2 | 14 | 71 |
| P85 | 4600 | 39.7 | 52.3 | 16 | 65 |
| F87 | 7700 | 39.8 | 122.5 | 24 | 91 |
| F88 | 11400 | 39.3 | 207.8 | 28 | 250 |
| L92 | 3650 | 50.3 | 16.6 | 6 | 88 |
| F98 | 13000 | 44.8 | 236.4 | 28 | 77 |
| L101 | 3800 | 58.9 | 8.6 | 1 | 2.1 |
| P103 | 4950 | 59.7 | 33.8 | 9 | 6.1 |
| P104 | 5900 | 61.0 | 53.6 | 13 | 3.4 |
| P105 | 6500 | 56.0 | 73.9 | 15 | 6.2 |
| F108 | 14600 | 50.3 | 265.4 | 27 | 22 |
| L121 | 4400 | 68.2 | 10.0 | 1 | 1 |
| P123 | 5750 | 69.4 | 39.2 | 8 | 4.4 |
| F127 | 12600 | 65.2 | 200.4 | 22 | 2.8 |

[a]The average numbers of oxyethylene and oxypropylene units were calculated using the average molecular weighs (MW) provided by the manufacturer. The hydrophilic-lipophilic balance (HLB) of the copolymers were determined by the manufacturer (BASF Co.). The critical micellization concentrations (CMC) were determined by the surface tension method described in Kabanov et al., Macromolecules 28: 2303–2314 (1995).

Some other specific poly(oxyethylene)-poly(oxypropylene) block copolymers relevant to the invention include:

| NN* | Block Copolymer | Hydrophobe Weight | Hydrophobe Percentage |
|---|---|---|---|
| 1 | F38 | 900 | 20% |
| 2 | L42 | 1200 | 80% |
| 3 | L63 | 1750 | 70% |
| 4 | P65 | 1750 | 50% |
| 5 | L72 | 2050 | 80% |
| 6 | F75 | 2050 | 50% |
| 7 | P77 | 2050 | 30% |
| 8 | L122 | 4000 | 80% |
| 9 | 10R5 | 1000 | 50% |
| 10 | 10R8 | 1000 | 20% |
| 11 | 12R3 | 1200 | 70% |
| 12 | 17R1 | 1700 | 90% |
| 13 | 17R2 | 1700 | 80% |
| 14 | 17R4 | 1700 | 60% |
| 15 | 17R8 | 1700 | 20% |
| 16 | 22R4 | 2200 | 60% |
| 17 | 25R1 | 2500 | 90% |
| 18 | 25R2 | 2500 | 80% |
| 19 | 25R4 | 2500 | 60% |
| 20 | 25R5 | 2500 | 50% |
| 21 | 25R8 | 2500 | 50% |
| 22 | 31R1 | 3100 | 90% |
| 23 | 31R2 | 3100 | 80% |
| 24 | 31R4 | 3100 | 60% |
| 25 | 304 | 500 | 60% |
| 26 | 504 | 1100 | 60% |
| 27 | 701 | 2200 | 90% |
| 28 | 702 | 2200 | 80% |
| 29 | 704 | 2200 | 60% |
| 30 | 707 | 2200 | 30% |
| 31 | 901 | 3300 | 90% |
| 32 | 904 | 3300 | 60% |
| 33 | 908 | 3300 | 20% |

-continued

| NN* | Block Copolymer | Hydrophobe Weight | Hydrophobe Percentage |
|---|---|---|---|
| 34 | 1101 | 4400 | 90% |
| 35 | 1102 | 4400 | 80% |
| 36 | 1104 | 4400 | 60% |
| 37 | 1107 | 4400 | 30% |
| 38 | 1301 | 5500 | 90% |
| 39 | 1302 | 5500 | 80% |
| 40 | 1304 | 5500 | 60% |
| 41 | 1307 | 5500 | 30% |
| 42 | 1501 | 7000 | 90% |
| 43 | 1502 | 7000 | 80% |
| 44 | 1504 | 7000 | 60% |
| 45 | 1508 | 7000 | 20% |
| 46 | 50R1 | 2100 | 90% |
| 47 | 50R4 | 2100 | 60% |
| 48 | 50R8 | 2100 | 20% |
| 49 | 70R1 | 3000 | 90% |
| 50 | 70R2 | 3000 | 80% |
| 51 | 70R4 | 3000 | 60% |
| 52 | 90R1 | 3900 | 90% |
| 53 | 90R4 | 3900 | 60% |
| 54 | 90R8 | 3900 | 20% |
| 55 | 110R1 | 4800 | 90% |
| 56 | 110R2 | 4800 | 80% |
| 57 | 110R7 | 4800 | 30% |
| 58 | 130R1 | 5700 | 90% |
| 59 | 130R2 | 5700 | 80% |
| 60 | 150R1 | 6700 | 90% |
| 61 | 150R4 | 6700 | 60% |
| 62 | 150R8 | 6700 | 20% |

*All block copolymers (1–8) conform to formula (V), all block copolymers (9–24) conform to formula (VII), all block copolymers (25–45) conform to formula (VIII), all block copolymers (46–62) conform to formula (IX).

The diamine-linked pluronic of formula (VIII) can also be a member of the family of diamine-linked polyoxyethylene-polyoxypropylene polymers of formula:

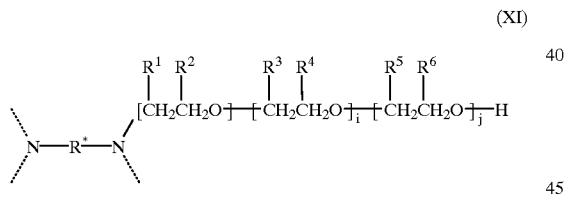

(XI)

wherein the dashed lines represent symmetrical copies of the polyether extending off the second nitrogen, R* an alkylene of about 2 to about 6 carbons, a cycloalkylene of about 5 to about 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen. The —NH$_2$—CH$_2$CH$_2$—NH$_2$— group of formula (VIII) and the N—R*—N group of formula (XI) are examples of linking groups, L, of formula (IV).

Those of ordinary skill in the art will recognize that even when the practice of the invention is confined for example, to poly(oxyethylene)-poly(oxypropylene) compounds, the above exemplary formulas are too confining. An important feature is that the average Hansch-Leo fragmental constant of the monomers in an A-type block be about –0.4 or less. Thus, the units making up the first block need not consist solely of ethylene oxide. Similarly, not all of the B-type block need consist solely of propylene oxide units. Instead, the blocks can incorporate monomers other than those defined in formulas (V)–(IX), so long as the parameters of the first embodiment are maintained. Thus, in the simplest of examples, at least one of the monomers in block A might be substituted with a side chain group as previously described.

In another aspect, the invention relates to a drug composition made up of a block copolymer at least one of formulas (I)–(X), wherein the A-type and B-type blocks are. substantially made up of repeating units of formula —O-$R^5$, where $R^5$ is:

(1) —(CH$_2$)$_n$—CH($R^6$)—, wherein n is zero or an integer from about 1 to about 5 and $R^6$ is hydrogen, cycloalkyl having about 3 to about 8 carbon atoms, alkyl having about 1 to about 6 carbon atoms, phenyl, alkylphenyl wherein the alkyl has about 1 to about 6 carbon atoms, hydroxy, hydroxyalkyl, wherein the alkyl has about 1 to about 6 carbon atoms, alkoxy having about 1 to about 6 carbon atoms, an alkyl carbonyl having about 2 to about 7 carbon atoms, alkoxycarbonyl, wherein the alkoxy has about 1 to about 6 carbon atoms, alkoxycarbonylalkyl, wherein the alkoxy and alkyl each independently has about 1 to about 6 carbon atoms, alkylcarboxyalkyl, wherein each alkyl independently has about 1 to about 6 carbon atoms, aminoalkyl wherein the alkyl has about 1 to about 6 carbon atoms, alkylamine or dialkylamino, wherein each alkyl independently has about 1 to about 6 carbon atoms, mono- or di-alkylaminoalkyl wherein each alkyl independently has about 1 to about 6 carbon atoms, chloro, chloroalkyl wherein the alkyl has from about 1 to about 6 carbon atoms, fluoro, fluoroalkyl wherein the alkyl has from about 1 to about 6 carbon atoms, cyano or cyano alkyl wherein the alkyl has from about 1 to about 6 carbon atoms or carboxyl;

(2) a carbocyclic group having about 3 to about 8 ring carbon atoms, wherein the group can be for example, cycloalkyl or aromatic groups, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substitutions, or (3) a heterocyclic group, having about 3 to about 8 ring atoms, which can include heterocycloalkyl or heteroaromatic groups, which can include from about 1 to about 4 heteroatoms selected from the group consisting of oxygen, nitrogen, sulfur and mixtures thereto, and which can include alkyl having about 1 to about 6 carbon atoms, alkoxy having about 1 to about 6 carbon atoms, alkylamino having about 1 to about 6 carbon atoms, dialkylamino wherein each alkyl independently has about 1 to about 6 carbon atoms, amino, sulfonyl, hydroxy, carboxyl, fluoro or chloro substitutions.

Preferably, n is an integer from about 1 to about 3. The carbocyclic or heterocyclic groups comprising R 5 preferably have from about 4 to about 7 ring atoms, more preferably about 5 about 6. Heterocycles preferably include from about 1 to about 2 heteroatoms, more preferably, the heterocycles have one heteroatom. Preferably, the heterocycle is a carbohydrate or carbohydrate analog.

Those of ordinary skill will recognize that the monomers required to make these polymers are synthetically available. See, Vaughn et al., *J. Am. oil Chem. Soc.* 28: 294 (1951). In some cases, polymerization of the monomers will require the use of suitable protective groups, as will be recognized by those of ordinary skill in the art. Generally, the A- and B-type blocks are at least about 80% comprised of —$OR^5$— repeating units, more preferably at least about 90%, yet more preferably at least about 95%.

In another aspect, the invention relates to a drug composition made up of a block copolymer of one of formulas (I)–(X) wherein the A-type and B-type blocks consist essentially of repeating units of formula –O-$R^7$, wherein $R^7$ is a $C_1$ to $C_6$ alkylene group.

The block copolymers of the invention will preferably form micelles in isotonic aqueous solutions at a physiological temperature having diameter from about 10 nm to about 100 nm. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a CMC that is characteristic of the amphiphile. By varying the sizes of the hydrophilic and hydrophobic segments of the block copolymers, the tendency of the copolymers to form micelles at physiological conditions, as well as the average size of the micelles formed at physiological conditions, can be varied. These tendencies can also be adjusted by blending copolymers with differing mixes of hydrophobic and hydrophilic blocks. The micelles have a dense core formed by the water insoluble repeating units of the B blocks and lipophilic portions of a biological agent dissolved therein, and a hydrophilic shell formed by the A blocks and hydrophobic portions of the biological agent. The micelles have translational and rotational freedom in aqueous environment, and aqueous environments containing the micelles have low viscosity similar to water. Micelle formation typically occurs at copolymer concentrations from about 0.001 to 5% (w/v).

The small size of the micelles formed by block copolymers of the invention is believed to allow these micelles to penetrate in small capillaries and to be taken up by cells. The micelles also can incorporate large amounts of appropriate biological agents.

The effective retention of a drug within the micelles of the invention can be quantified in terms of the partitioning coefficient (P) determined using formula:

$$P=[Agent]_m/[Agent]aq$$

where $(Agent]_{aq}$ is the concentration of biological agent in an aqueous environment outside of the micelles and $[Agent]_m$ is the concentration of agent in the micelles. In some cases, P is easily and accurately estimated based on the difference fluorescence properties of certain agents when in an aqueous versus a more hydrophobic environment.

Targeting

A minor portion of a targeting molecule made up of a targeting moiety coupled to a lipophilic moiety comprising a hydrocarbon having from about 3 to about 41 carbon atoms can be incorporated into the micelles of the compositions of the targeting embodiment of the invention. This portion typically comprises no more than about 10% w/w of the copolymer components of a composition. The lipophilic moieties are believed to act as hydrophobic "anchors," which are incorporated non-covalently into the block-copolymer micelles so that the targeting moiety becomes part of, but extends beyond, the micelle. Such targeting, moieties are preferably also incorporated into the micelles used in the targeting of the invention. However, for the targeting embodiment the lipophilic moiety can be any lipophilic moiety effective to non-covalently associate the targeting moiety with the micelles. For the targeting embodiment, the lipophilic moiety can be, for example a fatty acid residue, a lipid, phospholipid, or a natural or synthetic polymer. Because of availability and ease of use, lipophilic moieties containing hydrocarbon groups such as fatty acid residues are preferred.

The targeting moieties have affinity for a cellular, tissue, viral or substratum site. Typical targeting moieties include without limitation antibodies and hormones with affinity for a cellular binding component, any molecule containing a carbohydrate moiety recognized by a cellular binding component and drugs that bind to a cellular binding component. The phrase "binding component" includes both receptor and acceptor molecules. Preferably, the binding component is a cell-surface binding component. Both polyclonal and monoclonal antibodies which are either available commercially or described in the literature can be employed. Alternatively the ligand can be a naturally occurring protein, such as insulin, that binds to a target site. A non-limiting example of a targeting moiety is the anti-$\alpha_2$-GP antibody to brain glial cells ($\alpha_2$-glycoprotein) which is described by Slepnev et al., *Bioconjugate Chem.* 3:273–274 (1992).

To retain as much of the specificity of the polypeptide, preferably only one or two lipophilic moieties are bound to each polypeptide molecule. This binding can be achieved by the method described by Kabanov et al., *Protein Engineering*, 3:39–42 (1989), the contents of which are incorporated herein by reference. In this method the lipophilic moiety or a reactive analog thereof is reacted with the targeting moiety in the presence of the surfactant sodium bis(2-ethylhexyl)sulfosuccinate {AOT®}, octane and a small amount of water will form reversed micelles, that is micelles with water on the inside and octane on the outside. These reversed micelles serve as microreactors allowing uniform point modification of the polypeptide molecules with lipophilic moieties. Reactive derivatives of fatty acids such as stearoyl chloride or lauroyl chloride can be reacted with polypeptides or other hydrophilic targeting moieties using this reaction system. Because the reaction system allows for the level of fatty acyl substitution to be limited, greater biological activity and solubility of the targeting moiety is generally preserved.

Test Systems

The HIV-1 infected MT2 and H9 cell lines can be used to evaluate the effects of the block copolymers on biological active agents. While many human cell types are susceptible to HIV infection, the extent of infection varies greatly depending on cell type. In general, cells that possess CD4 receptors (CD4+ cells) are the most readily infected and most permissive for HIV replication. Such cells include, for example, T-lymphocytes and macrophages.

A variety of permanent established cell lines of lymphocte and monocyte/macrophage derivation can be used to propagate and maintain HIV in in vitro culture. These include the CD4+ MT2 and MT4 cell lines, which are cloned human T-lymphocytic cells isolated from adult T-cell leukemia patients. These cells are highly susceptible to HIV-induced cytopathic effects, and are useful for acute infection cytopathicity inhibition assays for antiviral drugs.

Other cells include the cloned H9 cell line, derived from a human cutaneous T-lymphoma patient. See Mann, DL et al., *AIDS Res Hum Retroviruses* 5:253 (1989). H9 cells are CD4+ and permissive for HIV infection, but are relatively non-susceptible to HIV-induced cytopathic effects. Once infected with HIV, these cells continuously produce new virus without succumbing to the infection. These infected cells, H9+, are said to be "chronically-infected" or "persistently-infected."

The steps of HIV replication up to the formation of proviral DNA can be considered "pre-integrational" stages, and those involved in the formation of nascent virions after integration of proviral DNA can be considered as "post-integrational". The MT2 and MT4 cell lines are useful to assess antiviral activity against pre-integrational stages of HIV replication (in particular, effects on viral reverse transcription). The H9+ cells are useful to examine antiviral activity against post-integrational stages of HIV replication, including effects on virus assembly, shedding and maturation.

Routes of Administration

Oral delivery is the preferred method of administration for the instant compositions. For oral administration, the compositions can be used in the form of tablets capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the compositions can be combined with emulsifying and suspending agents. If desired, certain sweetening and/or flavoring agents can be added.

The pharmaceutical compositions of the invention can also be administered by a number of other routes, including without limitation, topically, rectally, vaginally, by pulmonary route, for instance, by use of an aerosol, or parenterally, including but not limited to intramuscularly, subcutaneously, intraperitoneally, intra-arterially or intravenously. The compositions can be administered alone, or can be combined with a pharmaceutically-acceptable carrier or excipient according to standard pharmaceutical practice.

For parenteral administration, sterile solutions of the conjugate are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

Suppository forms of the compositions of the invention are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycol of various molecular weights and fatty acid esters of polyethylene glycol. See Remington's Pharmaceutical Sciences, 16th Ed., Mack Publishing, Easton, Pa., 1980, pp. 1530–1533 for further discussion of suppository dosage forms. Analogous gels or creams can be used for vaginal, urethral and rectal administrations.

The following examples will serve to further typify the nature of the invention but should not be construed as a limitation on the scope thereof, which is defined solely by the appended claims.

EXAMPLE 1

In vitro Inhibitory Activities of BBNH and Fe(III)-BBNH Complex

BBNH and Fe(III)-BBNH complex at various concentrations were examined for the ability to inhibit RNA dependent and DNA dependent DNA polymerase activities as well as RNAse H activity of HIV-1 reverse transcriptase (RT RDDP, RT DDDP, and RT RNAse H, respectively). To analyze RT RDDP and RT DDDP the following reaction mixture (100 µl total volume) was used: 50 mM Tris-HCl (pH 7.8), 60 mM KCl, 10 mM $MgCl_2$, 10 ng of p51/p66 RT, 0.1–0.5 units of template/primer, and 0.5–25 µM [$^3$H]dNTP. Aliquots of the test compounds dissolved in DMSO were added to the reaction mixtures, incubated for 10–20 min. at 37° C. and than quenched with 500 µl of cold 20 mM sodium pyrophosphate in 10% dichloroacetic acid. After 10 min. on ice, the samples were filtered on Whatman 934-AH glass fiber filters and washed with 10% dichloroacetic acid and ethanol, and the radioactivity was determined by liquid scintillation analysis. To analyze RT RNAse H the following reaction mixture (50 µl total volume) was used: 5OmM Tris-HCl (pH 8.0), 60 mM KCl, 8 mM $MgCl_2$, and variable amounts of ([$^3$H]rG)-poly(dC). Generally, 10 ng of p51/p66 heterodimeric RT per assay were used. Aliquots of the test compounds dissolved in DMSO were added to the reaction mixtures, incubated for 20 min. at 37° C. and than quenched by placing the tubes on ice followed by the addition of 100 µl of cold 7% perchloric acid. After 10 min. on ice, the samples were centrifuged at 12,000 g for 15 min. 100 µl of the supernatants were carefully removed, and the radioactivity was determined by liquid scintillation analysis. The results of the experiments are shown in Table 1.

TABLE 1

In vitro Inhibitory activities of BBNH and Fe(III)-BBNH complex

| Inhibitory activity | $IC_{50}$ (µM) BBNH | Fe(III)-BBNH | Ratio BBNH/Fe(III)-BBNH |
|---|---|---|---|
| RT RDDP | 1.9 ± 0.1 | 0.4 ± 0.08 | 4.8 |
| RT DDDP | 12.5 ± 5.0 | 0.9 ± 0.3 | 13.5 |
| RT RNase H No preincubation | >50 | 0.9 ± 0.5 | >50 |
| RT RNase H 10 min. preincubation | 3.5 ± 0.8 | 0.5 ± 0.07 | 7 |

EXAMPLE 2

Cytotoxic Activity of BBNH and Fe(III)-BBNH Complex

BBNH and Fe(III)-BBNH complex at various concentrations were examined for cytotoxic activity against uninfected MT2 cells. Aliquots of a solution of the compounds in dimethyl sulfoxide were added to the MT2 cells ($2\times10^5$ cells/ml) in RPMI medium containing 10% fetal bovine serum to provide defined final concentrations of test compound. The cells and test compounds were cultured for 4 days at 37° C., in the presence of 5% $CO_2$ and then cytotoxic effect of the compounds was analyzed by using the standard XTT assay. The $CC_{50}$ calculated from the results were 10±0.5 µM for BBNH and more than 1000 µM for Fe(III)-BBNH.

EXAMPLE 3

Inhibitory Activity of BBNH and Fe(III)-BBNH Complex Against HIV-1 Infection

BBNH and Fe(III)-BBNH complex at various concentrations were examined for the ability to inhibit HIV-1 infection of uninfected MT2 cells. Aliquots of a solution of the compounds in dimethyl sulfoxide were added to uninfected MT2 cells ($2 \times 10^5$ cells/ml) in RPMI medium containing 10% fetal bovine serum to provide defined final concentrations of test compound. The cells and test compounds were incubated for 30 minutes at 37° C., then inoculated with a suspension of HIV virions. The cells, test compounds and HIV were incubated for 18 h at 37° C., then the cells were collected by centrifugation, washed, and resuspended in RPMI medium containing 10% fetal bovine serum and containing the same concentration of test compound as initially employed. The cells were then cultured at 37° C. (with culture medium changes as required). HIV infection was assessed by microscopic examination of HIV-induced cytopathicity (syncytium) and/or by analysis of HIV p24 antigen levels in the culture supernatants. The $IC_{50}$ calculated from the results were $1.5 \pm 0.5$ $\mu$M for BBNH and more than 50 $\mu$M for Fe(III)-BBNH.

EXAMPLE 4

Solubility of Fe(III)-BBNH in Water and Organic Solvents

A. Calibration of Fe(III)BBNH solubility in DMSO.

One mg of Fe(III)BBNH was dissolved in 1 ml of dimethyl sulfoxide (DMSO). Aliquots of the solution were further diluted with DMSO to achieve the following final concentrations: 1000 mg/ml; 500 mg/ml; 200 mg/ml; 100 mg/ml; 40 mg/ml; 20 mg/ml; 10 mg/ml. Each concentration point of was prepared in triplicates. The aliquots (50 ml) of the samples were transferred in 96-well plate. The optical densities (OD) at 1,400 nm of all the samples were measured by using Microplate Reader. The results are shown in Table 2.

TABLE 2

Optical densities of Fe(III)BBNH solutions in DMSO

| Fe(III)BBNH, g/ml | Optical Density, 400 nm | Standard deviation |
|---|---|---|
| 0 | 0 | 0 |
| 10 | 0.026 | 0.0007 |
| 20 | 0.042 | 0.0044 |
| 40 | 0.092 | 0.0026 |
| 100 | 0.207 | 0.0032 |
| 200 | 0.435 | 0.0065 |
| 500 | 1.019 | 0.0150 |
| 1000 | 2.003 | 0.0656 |

B. Analysis of Fe3O6 concentrations in different organic solvents.

The samples of Fe(III)BBNH (1 mg each) were placed in 1 ml of the following solvents:

1) $H_2O$ 100%;
2) Acetonitrile 100%;
3) 90% Acetonitrile; 10% $H_2O$;
4) 80% Acetonitrile; 20% $H_2O$;
5) Methanol: 100%;
6) 90% Methanol; 10% $H_2O$;
7) DMFA 100%;
8) DMSO 100%;

The samples were intensively agitated during three hours at room temperature using a rotator. After that the samples were centrifuged at 10,000 g for 10 minutes. The supernatants (500 $\mu$l each) were separated and then were dried by using a speed-vac centrifuge. Each sample was then dissolved in 500 $\mu$l DMSO and aliquots (50 $\mu$l each) were transferred to 96-well plate. The optical densities were determined at $\lambda$400 nm for using microplate reader. Concentrations of the test compound in the samples were then determined by using the above shown calibration data. Each concentration of the test compound was measured in triplicates. The results are shown in Table 3.

TABLE 3

Fe(III)BBNH solubility in the organic solvents

| Solvent | Solubility of Fe(III)BBNH dissolved in the sample, $\mu$g/ml | Standard Deviation |
|---|---|---|
| Water 100% | <0.001 | |
| Acetonitrile: 100%; | 163.6 | 0.007 |
| Acetonitrile: 10% $H_2O$; | 491.4 | 0.010 |
| Acetonitrile: 20% $H_2O$; | 293.9 | 0.009 |
| Methanol: 100%; | 505.6 | 0.022 |
| Methanol: 10% $H_2O$; | 206.7 | 0.015 |
| DMFA 100%; | 1000.2 | 0.007 |
| DMSO 100%; | 1001.4 | 0.001 |

EXAMPLE 5

Effect of Various Salts and pH on Fe(I)BBNH Solubility in Organic Solutions

The samples of Fe(III)BBNH (1 mg of each) were placed in 1 ml of following range of solvents:

1) 90% Acetonitrile; 10% 0.01M Ammonium Acetate (in water) pH 7.0;
2) 90% Acetonitrile; 10% 0.01M Ammonium Acetate (in water) pH 5.0;
3) 90% Acetonitrile; 10% 0.01M Ammonium Acetate (in water) pH 3.0;
4) 90% Methanol; 10% 0.01M Ammonium Acetate (in water) pH 7.0;
5) 90% Methanol; 10% 0.01M Ammonium Acetate (in water) pH 5;
6) 90% Methanol; 10% 0.01M Ammonium Acetate (in water) pH 3;
7) 90% Acetonitrile; 10% 0.01M Ammonium Formate (in water) pH 6.2;
8) 90% Acetonitrile; 10% 0.01M Ammonium Formate (in water) pH 5;
9) 90% Acetonitrile; 10% 0.01M Ammonium Formate (in water) pH 3;
10) 90% Methanol; 10% 0.01M Ammonium Formate (in water) pH 6.2;
11) 90% Methanol; 10% 0.01 M Ammonium Formate (in water) pH 5.0;
12) 90% Methanol; 10% 0.01M Ammonium Formate (in water) pH 3.0;
13) 90% Methanol; 10% 0.01M phosphate buffer (in water) (0.01M) pH 3.0;
14) 90% Methanol; 10% 0.01M phosphate buffer (in water) pH 5.0;

The samples were intensively agitated during three hours at room temperature using a rotator. After that the samples were centrifuged at 10,000 g for 10 min. The supernatants (500 $\mu$l each) were separated and then dried by using a speed-vac centrifuge. Each sample was dissolved in 500 $\mu$l DMSO and the aliquots (50 $\mu$l each) were transferred to 96-well plate. The optical densities were determined at λ400 nm using a microplate reader. Fe(III)BBNH concentrations in the samples were then determined by using the calibration shown in Example 4A. Each concentration of Fe(III)BBNH was analyzed in triplicates. The results are summarized in Table 4.

TABLE 4

FE(III)BBNH Solubility in Different Organic Solutions in the Presence of Various Salts and at Various PH

| Solution | Concentration of Fe306 dissolved in the sample, µg/ml | Standard Deviation |
| --- | --- | --- |
| Acetonitrile:10% Ammonium Acetate (0.01 M) pH 7.0 | 304.7 | 0.006 |
| Acetonitrile:10% Ammonium Acetate (0.01 M) pH 5.0 | 223.9 | 0.006 |
| Acetonitrile:10% Ammonium Acetate (0.01 M) pH 3.0 | 125.7 | 0.008 |
| Methanol:10% Ammonium Acetate (0.01 M) pH 7.0 | 94.4 | 0.006 |
| Methanol:10% Ammonium Acetate (0.01 M) pH 5.0 | 76.6 | 0.003 |
| Methanol:10% Ammonium Acetate (0.01 M) pH 3.0 | 26.2 | 0.008 |
| Acetonitrile:10% Ammonium Formate (0.01 M) pH 6.2 | 200.1 | 0.015 |
| Acetonitrile:10% Ammonium Formate (0.01 M) pH 5.0 | 233.6 | 0.002 |
| Acetonitrile:10% Ammonium Formate (0.01 M) pH 3.0 | 172.9 | 0.009 |
| Methanol:10% Ammonium Formate (0.01 M) pH 6.2 | 31.2 | 0.002 |
| Methanol:10% Ammonium Formate (0.01 M) pH 5.0 | 43.4 | 0.014 |
| Methanol:10% Ammonium Formate (0.01 M) pH 3.0 | 50.9 | 0.003 |
| Methanol:10% 0.01 M phosphate buffer pH 3.0 | 14.4 | 0.007 |
| Methanol:10% 0.01 M phosphate buffer pH 5.0 | 14.9 | 0.001 |

EXAMPLE 6

Effect of Various Block Copolymers on Water Solubility of Fe(III)BBNH

The samples of Fe(III)BBNH (1 mg of each) were placed in 1 ml of various water solutions of Pluronics. The samples were intensively agitated during three hours at room temperature using a rotator. The samples were then centrifuged at 10,000g for 10 min. The supernatants (500 µl each) were separated and then dried using a speed-vac centrifuge. Each sample was dissolved in 500 µl DMSO and aliquots (50 µl each) were transferred to 96-well plate. The optical densities were determined at λ400 nm using a microplate. The test compound concentrations in the samples were then determined by using the calibration shown in Example 4A. Each concentration of Fe(III)BBNH was analyzed in triplicates. The results are summarized in Table 5. Each concentration of Fe306 was measured in triplicates.

TABLE 5

Fe(III)BBNH solubility in various Pluronic solutions

| Pluronic (concentration, % w/v) | Solubility of Fe(III)BBNH, µg/ml | Standard Deviation |
| --- | --- | --- |
| Pluronic L61(1%) | 3.5 | 0.03 |
| Pluronic L64(2%) | 996.6 | 1.5 |

TABLE 5-continued

Fe(III)BBNH solubility in various Pluronic solutions

| Pluronic (concentration, % w/v) | Solubility of Fe(III)BBNH, µg/ml | Standard Deviation |
| --- | --- | --- |
| Pluronic L44(2%) | 986.8 | 1.8 |
| Pluronic L81(2%) | 175.3 | 0.9 |
| Pluronic F87(2%) | 992.5 | 1.1 |
| Pluronic P84(1%) | 987.2 | 2.3 |
| Pluronic P85(1%) | 998.3 | 2.7 |
| Pluronic F108(2%) | 86.5 | 0.5 |
| Pluronic P123(2%) | 125.7 | 0.3 |
| Pluronic F127(2%) | 113.6 | 0.8 |

EXAMPLE 7

Effect of Concentration of Block Copolymer on Water Solubility of Fe(III)BBNH

Various amounts of Fe(III)BBNH were dissolved in 200 µl dimethyl formamide and aliquots (20 µl each) were mixed with the equal volumes of Pluronic P85 solutions of various concentrations in methanol. The water solution of sodium acetate (10 µl) was added to each sample to the final concentration of the salt of 60 mM. The samples were dried by using a speed-vac centrifuge. Each sample was dissolved in 100 µl of 10% Pluronic P85 solution in water. The samples were intensively agitated during two hours at room temperature using a rotator. After that the samples were centrifuged at 10,000 g for 10 min. The supernatants were separated and then diluted with 10% Pluronic P85 solution in water to fit the range of calibration curve. The aliquots (50 µl each) were transferred to 96-well plate and analyzed. The optical densities were determined at λ400 nm using a microplate reader. Fe(III)BBNH concentrations in the samples were then determined by using the calibration shown in Example 4A. Each concentration of Fe(III)BBNH was analyzed in triplicates. The results are summarized in Table 6. Each concentration of Fe306 was measured in triplicates.

TABLE 6

Solubility of Fe(III)BBHN in Pluronic P85 formulations

| Fe(III)BBHN Added, mg/ml | Fe(III)BBHN solubility in, mg/ml | | | | |
| --- | --- | --- | --- | --- | --- |
| | 1% P85 | 2% P85 | 3% P85 | 5% P85 | 10% P85 |
| 1 | 1.12 | 1.13 | 1.04 | 1.09 | 1.08 |
| 2 | 2.12 | 2.16 | 2.24 | 2.08 | 2.06 |
| 5 | 1.4 | 5.02 | 5.06 | 5.09 | 5.16 |
| 10 | 1.39 | 3.1 | 7.42 | 10.51 | 10.71 |
| 20 | 0.73 | 2.71 | 5.15 | 10.36 | 19.06 |
| 30 | 0.01 | 2.39 | 5.14 | 12.25 | 22.87 |
| 40 | 0.03 | 0.42 | 2.96 | 10.48 | 26.24 |

EXAMPLE 8

Effect of Test Compounds on Inhibition of HIV-1 Acute Infection of MT2 Cells

Formulations containing compound I were examined for the ability to inhibit HIV-1 infection of uninfected MT2 cells, in comparison with compound I alone. Aliquots of a solution of compound I in dimethyl sulfoxide or an aqueous solution of the copolymer-compound I formulation were added to uninfected MT2 cells ($2 \times 10^5$ cells/ml) in RPMI medium containing 10% fetal bovine serum to provide defined final concentrations of test compound. The cells and test compounds were incubated for 30 minutes at 37° C., then inoculated with a suspension of HIV virions. The cells, test compounds and HIV were incubated for 18 h at 37° C., then the cells were collected by centrifugation, washed, and resuspended in RPMI medium containing 10% fetal bovine serum and containing the same concentration of test compound as initially employed. The cells were then cultured at 37° C. (with culture medium changes as required). HIV infection was assessed by microscopic examination of HIV-induced cytopathicity (syncytium) and/or by analysis of HIV p24 antigen levels in the culture supernatants. The results of the experiment showed that compound I dissolved in DMSO did not reveal any significant activity at the concentrations up to 25 $\mu$M, while $IC_{50}$ of the copolymer formulated compound was 4.8±0.4 $\mu$M. In some experiments, test compounds and HIV-1 virions were added simultaneously to the uninfected MT2 cells; results were similar to those of experiments in which test compound was added to the cells for 30 minutes prior to addition of HIV virions.

EXAMPLE 9

Incubation of HIV-1 Chronically-infected H9 cells (H9+) with Copolymer Biological Agent Formulations: Effect on Infectivity of HIV Virions Formulations containing compound I were examined for the ability to inhibit effects on the infectivity of HIV virions produced from H9+ cells, in comparison with compound I alone. Aliquots of a solution of compound I in dimethyl sulfoxide or an aqueous solution of the copolymer-compound I formulation were added to chronically-infected H9 cells (H9+; 5×10$^5$ cells/ml) in RPMI medium containing 10% fetal bovine serum to provide defined final concentrations of test compound. The cells and test compounds were incubated for 18 h 37° C., then the cells and the HIV virions produced were separated by centrifugation at 750×g. Aliquots of the supernatants (which contained the HIV virions) were added to uninfected MT2 cells (2×10$^5$ cells/ml) in RPMI medium containing 10% fetal bovine serum. The cells and HIV virions were incubated for 18 h at 37° C., then the cells were collected by centrifugation, washed, and resuspended in RPMI medium containing 10% fetal bovine serum without test compound. The cells were then cultured at 37° C. (with culture medium changes as required). HIV infection was assessed by microscopic examination of HIV-induced cytopathicity (syncytium) and/or by analysis of HIV p24 antigen levels in the culture supernatants. The results of the experiment showed that compound I dissolved in DMSO did not reveal any significant activity at the concentrations up to 10 $\mu$M, while $IC_{50}$ of the copolymer formulated compound was 0.1±0.05 $\mu$M.

EXAMPLE 10

Incubation of HIV-1 Chronically-Infected H9 Cells (H9+) with Copolymer—Biological Agent Formulations: Effect on Cell-to-Cell Transmission of HIV Formulations containing compound I were examined for the ability to inhibit cell-to-cell transmission of HIV produced from H9+ cells to uninfected MT2 cells, in comparison with compound I alone. Aliquots of a solution of compound I in dimethyl sulfoxide or an aqueous solution of the copolymer-compound I formulation were added to chronically-infected H9 cells (H9+; 5×10$^5$ cells/ml) in RPMI medium containing 10% fetal bovine serum to provide defined final concentrations of test compound. The cells and test compounds were incubated for 18 h 37° C., then the cells were isolated by centrifugation at 750×g, and washed several times by re-suspension in RPMI medium containing 10% fetal bovine serum followed by centrifugation. The cells were finally suspended in RPMI medium containing 10% fetal bovine serum, without test compound. Aliquots of these H9+ cells were added to uninfected MT2 cells (3×10$^5$ cells/ml) in RPMI medium containing 10% fetal bovine serum, to provide a final MT2:H9+ cell ratio of 30:1. The cells were then cultured at 37° C. (with culture medium changes as required). HIV infection was assessed by microscopic examination of HIV-induced cytopathicity (syncytium) of MT2 cells, and/or by analysis of HIV p24 antigen levels in the culture supernatants. The results of the experiment showed that compound I dissolved in DMSO did not reveal any significant activity at the concentrations up to 25 $\mu$M, while $IC_{50}$ of the copolymer formulated compound was 2.5±0.05 $\mu$M.

EXAMPLE 11

Prophylactic Effect of Test Compounds: Effect of Pretreatment of Uninfected MT2 Cells on Subsequent HIV Infection Formulations containing compound I were examined for the ability to protect uninfected MT2 cells from infection by isolated HIV virions, in comparison with compound I alone. Aliquots of a solution of compound I in dimethyl sulfoxide or an aqueous solution of the copolymer-compound I formulation were added to uninfected MT2 cells (3×10$^5$ cells/ml) in RPMI medium containing 10% fetal bovine serum to provide defined final concentrations of test compound. The cells and test compounds were incubated for 24 h 37° C., then the cells were isolated by centrifugation at 750×g, and washed several times by re-suspension in RPMI medium containing 10% fetal bovine serum followed by centrifugation. The cells were finally suspended in RPMI medium containing 10% fetal bovine serum, without test compound. Aliquots of HIV virions were added and the cells were then cultured at 37° C. (with culture medium changes as required). HIV infection was assessed by microscopic examination of HIV-induced cytopathicity (syncytium) of MT2 cells, and/or by analysis of HIV p24 antigen levels in the culture supernatants. The results of the experiment showed that compound I dissolved in DMSO did not reveal any significant activity at the concentrations up to 10 $\mu$M, while $IC_{50}$ of the copolymer formulated compound was 0.8±0.03 $\mu$M.

EXAMPLE 12

Micelle Size of Block Copolymers

Block copolymers of poly(oxyethylene)-poly (oxypropylene) having the ratios of poly(oxypropylene) to poly(oxyethylene) indicated below were dispersed in RPMI 1640 medium at the concentrations indicated below. The mixtures were incubated for 40 minutes at 300° C. The average micelle diameter was measured by quasielastic light scattering. See Kabanov et al., *Macromolecules* 28: 23032314, 1995. The results are shown in Table 7.

TABLE 7

| Copolymer | Conc. (% w/v) | Avg. Diameter |
|---|---|---|
| F-68 | 1.0% | 726.0 nm |
| P-85 | 1.0% | 18.0 nm |
| L-64 | 1.0% | 20.4 nm |
| 1:1.5 P-85:L-64 | 0.01% | 17.0 nm |
| 1:2.5 F-68:L-64 | 1.0% | 33.5 nm |

EXAMPLE 13

Acute Toxicity of Block Copolymers

The acute toxicity of Pluronic F108, P85 and L61 were studies in 5-week old BALB/c male mice. Each experimental group of mice included 6 mice.

Various doses of isotonic Pluronic solutions were administered i.p. Animal mortality was monitored daily for 14 days. The $LD_{50}$ and maximum tolerated dosage ("MTD", i.e., the dose at which no animals among 6 equivalently treated animals died) were calculated by probit analysis. See, Chan and Hayes in *Principles and Methods of Toxicology*, Hayes, A. W., ed., Raven Press, New York, 1989, pp. 169–189. The results are shown in Table 8.

TABLE 8

| Pluronic | MTD, g/kg | $LD_{50}$, g/kg |
|---|---|---|
| Pluronic L61 | 0.1 | 0.8 |
| Pluronic P85 | 0.2 | 0.8 |
| Pluronic F108 | 5.0 | 9.0 |

EXAMPLE 14

Solution Behavior of Poly(oxyethylene)-Poly(oxypropylene) Block Copolymers

Poly(oxyethylene)-poly(oxypropylene) block copolymers were dissolved in the phosphate-buffered saline, 10 μM, pH 7.4 (PBS) or in 2.5% solution of bovine serum albumin (BSA) in PBS at the concentrations shown below, and the mixtures incubated for at least one hour at 22.5° C. or 370° C. After that the effective diameters of the aggregates formed in these systems were measured by quasielastic light scattering method as described by Kabanov et al., *Macromolecules* 28, 2303–2314 (1995). The results are shown in Table 9.

TABLE 9

| Copolymer | Conc., % | T, °C. | Effective diameter, nm −BSA | Effective diameter, nm +BSA | Comments |
|---|---|---|---|---|---|
| Pluronic L61 | 0.05 | 22.5 | ND | 10.6 | |
|  | 0.1 | 22.5 | ND | 23.4 | |
|  | 0.25 | 22.5 | ND | 48.8 | |
|  | 0.5 | 22.5 | ND | 138.3 | |
|  | 0.005 | 37 | ND | 138 | |
| Pluronic L61 | 0.006 | 37 | ND | — | |
|  | 0.008 | 37 | 336 | — | |
|  | 0.01 | 37 | 455 | 120 | |
|  | 0.025 | 37 | 960 | (*) | |
|  | 0.04 | 37 |  | (*) | |
|  | 0.05 | 37 | 1265 | (*) | |
|  | 0.075 | 37 | 1120 | (*) | |
|  | 0.1 | 37 | LPS | LPS | |
|  | 0.25 | 37 | LPS | LPS | |
|  | 0.5 | 37 | LPS | LPS | |
| Pluronic L81 | 0.04 | 22.5 | — | 13.8 | |
|  | 0.1 | 22.5 | ND | 20.6 | |
|  | 0.25 | 22.5 | ND | 379 | Very cloudy solution with BSA |
|  | 0.5 | 22.5 | 935 | — | Very cloudy solutions |
|  | 0.01 | 37 | — | 266 | |
|  | 0.04 | 37 | 1004 | (*) | |
|  | 0.06 | 37 | (*) | (*) | |
|  | 0.08 | 37 | (*) | (*) | |
| Pluronic L121 | 22.5 | 0.01 | — | 541.5 | |
|  | 22.5 | 0.05 | — | 330 | |
| Pluronic F44 | 22.5 | 0.5 | ND | 12.9 | |
|  | 22.5 | 1.0 | ND | 11.7 | |
|  | 22.5 | 2.25 | ND | 14.2 | |
|  | 22.5 | 4.5 | ND | 28.7 | |
|  | 22.5 | 7.5 | ND | — | |
|  | 22.5 | 10.0 | ND | 105 | |
|  | 37 | 0.5 | ND | 84.4 | |
|  | 37 | 1.0 | ND | 97.1 | |
|  | 37 | 2.25 | ND | 137 | |
|  | 37 | 5.0 | ND | 68.1 | |
|  | 37 | 7.5 | ND | — | |
|  | 37 | 10.0 | 12.3 | 69.4 | |
| Pluronic L64 | 0.5 | 22.5 | ND | 10.8 | |
|  | 1.0 | 22.5 | ND | 12 | |
|  | 5.0 | 22.5 | ND | 21.6 | Opalescence and smell fraction of aggregates (85 nm) with BSA |
|  | 0.1 | 37 | ND | 36.2 | |
|  | 0.5 | 37 | 240 | 192.5 | Slightly cloudy solution without BSA and very cloudy solution with BSA |
|  | 1.0 | 37 | 16.6 | 11.6 | |
|  | 5.0 | 37 | 13.1 | 11.3 | |
| Pluronic P85 | 22.5 | 0.5 | ND | — | |
|  | 22.5 | 1.0 | ND | 12.9 | |
|  | 22.5 | 5.0 | ND | 18.7 | |
|  | 37 | 0.5 | 13.9 | — | |
|  | 37 | 1.0 | 12.6 | 79.6 | |
|  | 37 | 5.0 | 12.8 | 109 | |
| Pluronic F108 | 37 | 2.0 | — | 22.8 | — |
| Pluronic F127 | 37 | 1.0 | — | 23.2 | — |
|  | 37 | 2.0 | — | 21.5 | — |
| Tetronic T1307 | 22.5 | 2.0 | — | ND | — |
|  | 37 | 0.5 | — | 16.7 | — |
|  | 37 | 1.0 | — | 17.1 | — |
|  | 37 | 2.0 | — | 16.6 | 37.4 |

"ND": Non Detectable
"LPS": Liquid Phase Separation.
(*)Turbidity was too high for light scattering measurements.

These result suggest that (1) hydrophobic poly(ethylene oxide)-poly(propylene oxide) block copolymers with propylene oxide content not less than 50% (w/v) reveal tendency for aggregation in aqueous solutions at physiological temperature, (2) aggregation and phase separation of these copolymers is significantly enhanced in the presence of serum proteins.

EXAMPLE 15

Effects of Hydrophilic Pluronic Copolymers on Solution Behavior of Hydrophobic Pluronic Copolymers The same procedure as in Example 34 was used, but substituting a mixture of two different poly(ethylene oxide)-poly(propylene oxide) block copolymers for the results are shown in Table 10.

TABLE 10

| First Copolymer (conc. %) | Second conc., % | T, °C. | Effective diameter, nm −BSA | +BSA |
|---|---|---|---|---|
| Pluronic L121 | Pluronic F127 (0.5) | 22.5 | 116.4 | |
| | Pluronic F127 (1.0) | 22.5 | 113.9 | |
| | Pluronic F127 (5.0) | 22.5 | 313.2 | |
| | Pluronic F127 (0.5) | 37 | 88.7 | |
| Pluronic L121 (0.1) | Pluronic F127 (1.0) | 37 | 77.1 | |
| | Pluronic F127 (2.0) | 37 | 177 | |
| | Pluronic F127 (5.0) | 37 | 262 | |
| Pluronic L61 (0.1) | Pluronic F127 (0.5) | 37 | 26.7 | 23.8 |
| | Pluronic F127 (1.0) | 37 | 23.6 | 12.9 |
| | Pluronic F127 (2.0) | 37 | 21.6 | 13.8 |
| Pluronic L61 (0.125) | Pluronic F127 (1.0) | 37 | 24.7 | 53 |
| | Pluronic F127 (2.0) | 37 | 22.3 | — |
| Pluronic L61 (0.25) | Pluronic F127 (0.5) | 37 | (*) | — |
| | Pluronic F127 (1.0) | 37 | (*) | — |
| | Pluronic F127 (2.0) | 37 | 22.4 | 15.0 |
| Pluronic L61 (0.25) | Pluronic F108 (2.0) | 37 | 840 | — |
| Pluronic L61 (0.1) | Tetronic T1307 (1.0) | 37 | (*) | — |
| | Tetronic T1307 (1.5) | 37 | 915.4 | — |
| | Tetronic T1307 (2.0) | 37 | 16.3 | 624.8 |
| Pluronic L61 (0.15) | Tetronic T1307 (2.0) | 37 | 387.4 | — |
| Pluronic L61 (0.2) | | 37 | 520 | — |
| Pluronic L61 (0.25) | | 37 | 735.3 | — |
| Pluronic L61 (0.1) | Tetronic T1307 (2.5) | 37 | — | 522.3 |
| | Tetronic T1307 (3.0) | 37 | | 225 |
| | Tetronic T1107 (2.0) | 37 | (*) | |

"ND": Non-Detectable.
(*)Turbidity was too high for light scattering measurements.

These results suggest that (1) hydrophilic poly(oxyethylene)-poly(oxypropylene) block copolymers with ethylene oxide content more than 50% (w/v) prevent aggregation of hydrophobic hydrophilic Poly(oxyethylene)-poly(oxypropylene) block copolymers with propylene oxide content not less than 50% (w/v) at physiological temperatures; (2) hydrophilic poly(oxyethylone)-poly(oxypropylene) block copolymers with ethylene oxide content more than 50% (w/v) prevent aggregation of hydrophobic hydrophilic poly(oxyethylene)-poly(oxypropylene) block copolymers with propylene oxide content not less than 50% in the presence of serum proteins.

What is claimed is:

1. An antiviral pharmaceutical composition comprising an N-aroyl hydrazone and the metal according to the formula:

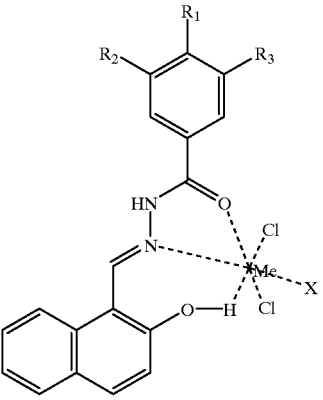

wherein $R_1$, $R_2$ and $R_3$ are H, OH, $CH_3$, $OCH_3$, $C(CH_3)_3$ [-tert-butyl], phenyl, and X is $—OCH_3$ or $—OCH_2CH_3$.

2. The composition according to claim 1 wherein the Me is Fe(III).

3. The composition according to claim 1 wherein $R_1$ is $—C(CH_3)_3$, $R_2$ and $R_3$ are hydrogen, Me is Fe(III), and X is $—OCH_3$.

4. The pharmaceutical composition according to the claim 1 further comprising a nonionic or zwitterionic surfactant.

5. The pharmaceutical composition according to the claim 2 where the surfactant is a nonionic block copolymer.

6. The pharmaceutical composition according to the claim 3 where the nonionic block copolymer is poly(oxyethylene)-poly(oxypropylene).

7. The pharmaceutical composition according to the claim 4 where the preferred content of poly(oxypropylene) block is about 50% of the poly(oxyethylene)poly(oxypropylene) molecule.

8. A method of treating HIV infection comprising administering to a mammal an effective amount of a composition according to claim 1.

* * * * *